(12) United States Patent
Rieping et al.

(10) Patent No.: US 7,052,883 B2
(45) Date of Patent: May 30, 2006

(54) PROCESS FOR THE PRODUCTION OF L-AMINO ACIDS USING STRAINS OF THE FAMILY ENTEROBACTERIACEAE THAT CONTAIN AN ATTENUATED FRUR GENE

(75) Inventors: Mechthild Rieping, Bielefeld (DE); Thomas Hermann, Bielefeld (DE)

(73) Assignee: Degussa AG, Duesseldorf (DE)

( * ) Notice: Subject to any disclaimer, the term of this patent is extended or adjusted under 35 U.S.C. 154(b) by 299 days.

(21) Appl. No.: 10/114,073

(22) Filed: Apr. 3, 2002

(65) Prior Publication Data

US 2003/0049803 A1 Mar. 13, 2003

Related U.S. Application Data

(60) Provisional application No. 60/283,384, filed on Apr. 13, 2001.

(30) Foreign Application Priority Data

Apr. 3, 2001 (DE) ................................. 101 16 518

(51) Int. Cl.
  *C12P 13/04* (2006.01)
(52) U.S. Cl. ..................... 435/106; 435/115; 435/106
(58) Field of Classification Search ................ 435/106, 435/115
  See application file for complete search history.

(56) References Cited

U.S. PATENT DOCUMENTS 4,278,765 A  7/1981  Debabov et al.

FOREIGN PATENT DOCUMENTS

| EP | 0 237 819 | 9/1987 |
|---|---|---|
| EP | 0 643 135 | 3/1995 |
| EP | 0 952 221 | 10/1999 |
| EP | 0 955 368 | 11/1999 |
| JP | 03-236786 | 11/1991 |
| WO | WO 99/53035 | 10/1999 |
| WO | WO 02/081721 | 10/2002 |
| WO | WO 02/081722 | 10/2002 |

OTHER PUBLICATIONS

Saier et al. The Carabolite Repressor/Activator (Cra) Protein of Enteric Bacteria. J. Bacteriol. (1996) 178(12): 3411-3417.*
T. M. Ramseier, et al., Research in Microbiology, vol. 147, No. 6-7, pp. 489-493, "CRA and the Control of Carbon Flux via Metabolic Pathways", Jul. 1996.
K. Jahreis, et al., Molecular and General Genetics, vol. 226, No. 1/2, pp. 332-336, "Nucleotide Sequence of the *ilvH-fruR* Gene Region of *Escherichia coli* K12 and *Salmonella typhimurium* LT2", Apr. 1991.
G. Michal, pp. 43-54, "Biochemical Pathways: An Atlas of Biochemistry and Molecular Biology", 1999.
R. Kraemer, Journal of Biotechnology, vol. 45, No. 1, pp. 1-21, "Genetic and Physiological Approaches for the Production of Amino Acids", 1996.
M. S M. Jetten, et al., Critical Reviews in Biotechnology, vol. 15, No. 1, pp. 73-103, "Recent Advances in the Physiology and Genetics of Amino Acid-Producing Bacteria", 1995.
G. Sawers, Archives of Microbiology, vol. 171, No. 1, pp. 1-5, "The Anaerobic Degradation of L-Serine and L-Threonine in Enterobacteria Networks of Pathways and Regulatory Signals", 1998.

* cited by examiner

Primary Examiner—Kathleen M. Kerr
Assistant Examiner—Hope Robinson
(74) Attorney, Agent, or Firm—Oblon, Spivak, McClelland, Maier & Neustadt, P.C.

(57) ABSTRACT

The invention relates to a process for producing an L-amino acid, in particular, L-threonine, which comprises: cultivating a microorganism of the family Enterobacteriaceae producing the desired L-amino acid under conditions suitable for production of the amino acid, in which the fruR (cra) (fructose repressor) gene or nucleotide secluences coding therefor in the microorganism is attenuated, in particular are switched off or eliminated, and recovering the L-amino acid from the medium or in the cells of the microorganism.

18 Claims, 1 Drawing Sheet

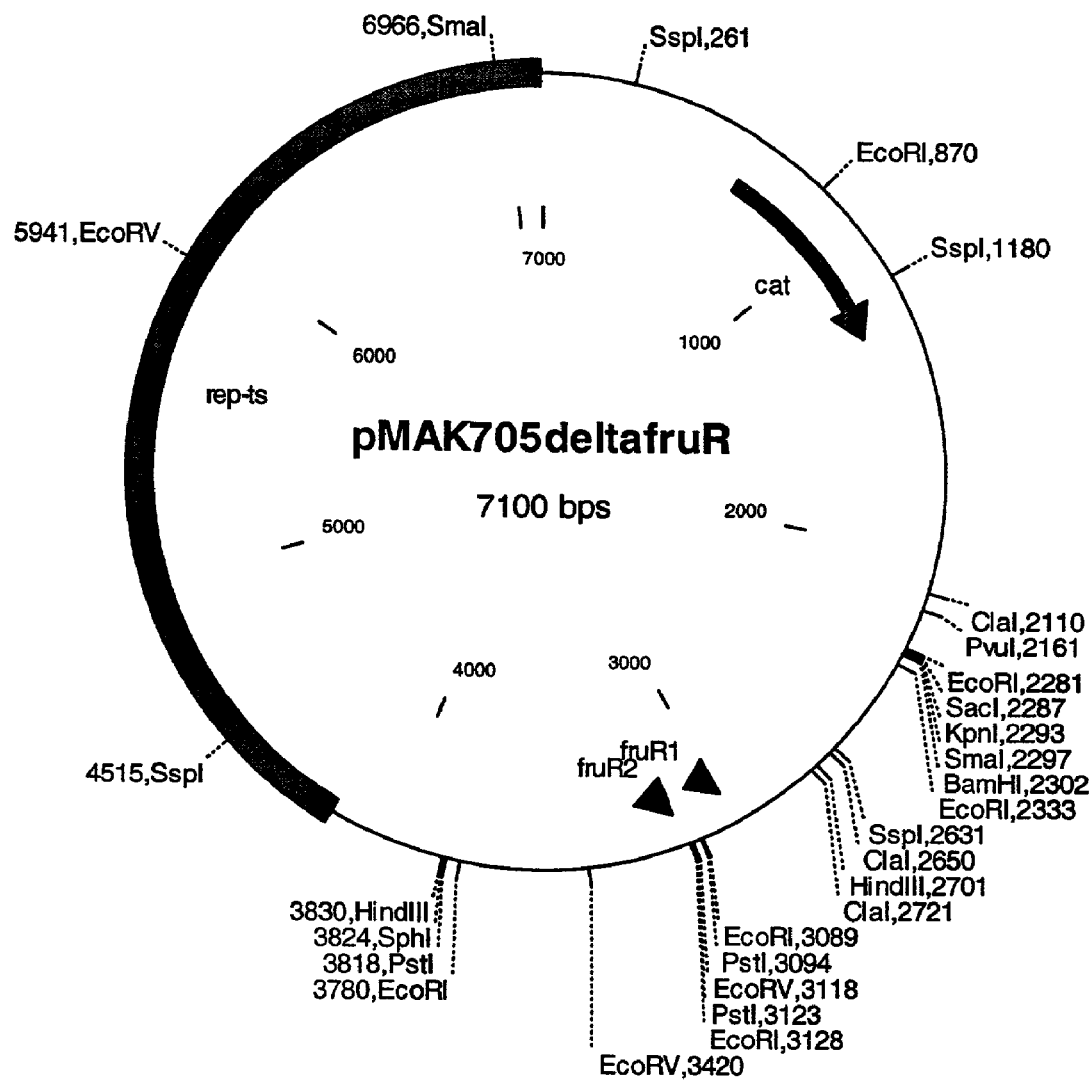

PROCESS FOR THE PRODUCTION OF L-AMINO ACIDS USING STRAINS OF THE FAMILY ENTEROBACTERIACEAE THAT CONTAIN AN ATTENUATED FRUR GENE

CROSS-REFERENCE TO RELATED APPLICATIONS

The present application claims priority to U.S. Provisional Application Ser. No. 60/283,384, filed Apr. 13, 2001, the contents of which are incorporated herein by reference.

FIELD OF THE INVENTION

The present invention relates to a process for the enzymatic production of L-amino acids, in particular L-threonine, using strains of the family Enterobacteriaceae in which the fruR gene is attenuated.

DESCRIPTION OF THE BACKGROUND

L-amino acids, in particular L-threonine, are used in human medicine and in the pharmaceutical industry, in the foodstuffs industry, and most especially in animal nutrition. It is known to produce L-amino acids by fermentation of strains of Enterobacteriaceae, in particular *Escherichia coli* (*E. coli*) and *Serratia marcescens*. On account of their great importance efforts are constantly being made to improve processes for producing the latter. Process improvements may relate to fermentation technology measures, such as for example stirring and provision of oxygen, or the composition of the nutrient media, such as for example the sugar concentration during the fermentation, or the working-up to the product form, for example by ion exchange chromatography, or the intrinsic performance properties of the microorganism itself.

Methods comprising mutagenesis, selection and mutant choice are employed in order to improve the performance properties of these microorganisms. In this way strains are obtained that are resistant to antimetabolites, such as for example the threonine analogue a-amino-β-hydroxyvaleric acid (AHV) or are auxotrophic for regulatorily important metabolites, and that produce L-amino acids such as for example L-threonine.

Methods of recombinant DNA technology have also been used for some years in order to improve strains of the family Enterobacteriaceae producing L-amino acids, by amplifying individual amino acid biosynthesis genes and investigating their effect on production.

SUMMARY OF THE INVENTION

The object of the invention is to provide new measures for the improved enzymatic production of L-amino acids, in particular L-threonine.

The present invention is based on the discovery microorganisms of the family Enterobacteriaceae which naturally produce L-amino acids do so more effectively under conditions in which the nucleotide sequence coding for the fruR gene is attenuated.

Thus, the object of the present invention may be accomplished with a process for the production of an L-amino acid, comprising:

(a) fermenting a microorganism of the family Enterobacteriaceae which produces the desired L-amino acid, in which the FruR gene or nucleotide sequences coding therefor are attenuated, in a medium;

(b) enriching the medium or the cells of the microorganism in the L-amino acid, and (c) isolating the L-amino acid.

A more complete appreciation of the invention and many of the attendant advantages thereof will be readily obtained as the same becomes better understood by reference to FIG. 1 and the following detailed description.

BRIEF DESCRIPTION OF THE DRAWINGS

FIG. 1: pMAK705ΔfruR (=pMAK705deltafruR)

Length data are given as approximate values. The abbreviations and acronyms used have the following meanings:

| | |
|---|---|
| cat: | chloramphenicol resistance gene |
| rep-ts: | temperature-sensitive replication region of the plasmid pSC101 |
| fruR1: | part of the 5' region of the fruR gene and the upstream-lying region |
| fruR2: | part of the 3' region of the fruR gene and the downstream-lying region |

The abbreviations for the restriction enzymes have the following meanings:

| | |
|---|---|
| BamHI: | restriction endonuclease from *Bacillus amyloliquefaciens* |
| BglII: | restriction endonuclease from *Bacillus globigii* |
| ClaI: | restriction endonuclease from *Caryphanon latum* |
| EcoRI: | restriction endonuclease from *Escherichia coli* |
| EcoRV: | restriction endonuclease from *Escherichia coli* |
| HindIII: | restriction endonuclease from *Haemophilus influenzae* |
| KpnI: | restriction endonuclease from *Kiebsiella pneumoniae* |
| PstI: | restriction endonuclease from *Providencia stuartii* |
| PvuI: | restriction endonuclease from *Proteus vulgaris* |
| SacI: | restriction endonuclease from *Streptomyces achromogenes* |
| SalI: | restriction endonuclease from *Streptomyces albus* |
| SmaI: | restriction endonuclease from *Serratia marcescens* |
| SphI: | restriction endonuclease from *Streptomyces phaeochromogenes* |
| SspI: | restriction endonuclease from *Sphaerotilus species* |
| XbaI: | restriction endonuclease from *Xanthomonas badrii* |
| XhoI: | restriction endonuclease from *Xanthomonas holcicola* |

DETAILED DESCRIPTION OF THE INVENTION

Where L-amino acids or amino acids are mentioned hereinafter, this is understood to mean one or more amino acids including their salts, selected from the group comprising L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-threonine is particularly preferred. Homoserine is another amino acid which may be enzymatically produced by the process of the present invention.

The term "attenuation" describes in this connection the reduction or switching off of the intracellular activity of one or more enzymes (proteins) in a microorganism that are coded by the corresponding DNA, by using for example a weak promoter or a gene or allele that codes for a corresponding enzyme with a low activity and/or that inactivates the corresponding enzyme (protein) or gene, and optionally combining these measures.

By means of these attenuation measures the activity or concentration of the corresponding protein is generally reduced to 0 to 75%, 0 to 50%, 0 to 25%, 0 to 10% or 0 to 5% of the activity or concentration of the wild type protein, or the activity or concentration of the protein in the initial microorganism.

The process is characterized in that the following steps are carried out:
  (a) fermentation of microorganisms of the family Enterobacteriaceae in which the fruR gene is attenuated,
  (b) enrichment of the corresponding L-amino acid in the medium or in the cells of the microorganisms of the family Enterobacteriaceae, and
  (c) isolation of the desired L-amino acid, in which optionally constituents of the fermentation broth and/or the biomass in its entirety or parts thereof remain in the product.

The microorganisms that are the subject of the present invention can produce L-amino acids from glucose, sucrose, lactose, fructose, maltose, molasses, optionally starch, optionally cellulose or from glycerol and ethanol. The microorganisms are members of the family Enterobacteriaceae selected from the genera *Escherichia, Erwinia, Providencia* and *Serratia*. The genera *Escherichia* and *Serratia* are preferred. In the case of the genus *Escherichia* the species *Escherichia coli* may in particular be mentioned, and in the case of the genus *Serratia* the species *Serratia marcescens* may in particular be mentioned.

Suitable strains of the genus *Escherichia*, in particular those of the species *Escherichia coli*, that produce in particular L-threonine, include for example:
  *Escherichia coli* TF427
  *Escherichia coli* H4578
  *Escherichia coli* KY10935
  *Escherichia coli* VNIIgenetika MG442
  *Escherichia coli* VNIIgenetika M1
  *Escherichia coli* VNIIgenetika 472T23
  *Escherichia coli* BKIIM B-3996
  *Escherichia coli* kat 13
  *Escherichia coli* KCCM-10132

Suitable strains of the genus *Serratia*, in particular of the species *Serratia marcescens*, that produce L-threonine include for example:
  *Serratia marcescens* HNr21
  *Serratia marcescens* TLr156
  *Serratia marcescens* T2000

Strains of the family of Enterobacteriaceae producing L-threonine preferably have, inter alia, one or more of the genetic or phenotype features selected from the following group: resistance to a-amino-β-hydroxyvaleric acid, resistance to thialysine, resistance to ethionine, resistance to a-methylserine, resistance to diaminosuccinic acid, resistance to a-aminobutyric acid, resistance to borrelidin, resistance to rifampicin, resistance to valine analogues such as for example valine hydroxamate, resistance to purine analogues such as for example 6-dimethylaminopurine, need for L-methionine, optionally partial and compensatable need for L-isoleucine, need for meso-diaminopimelic acid, auxotrophy with regard to threonine-containing dipeptides, resistance to L-threonine, resistance to L-homoserine, resistance to L-lysine, resistance to L-methionine, resistance to L-glutamic acid, resistance to L-aspartate, resistance to L-leucine, resistance to L-phenylalanine, resistance to L-serine, resistance to L-cysteine, resistance to L-valine, sensitivity to fluoropyruvate, defective threonine dehydrogenase, optionally ability to utilise sucrose, enhancement of the threonine operon, enhancement of homoserine dehydrogenase, I-aspartate kinase I, preferably of the feedback-resistant form, enhancement of homoserine kinase, enhancement of threonine synthase, enhancement of aspartate kinase, optionally of the feedback-resistant form, enhancement of aspartate semialdehyde dehydrogenase, enhancement of phosphoenol pyruvate carboxylase, optionally of the feedback-resistant form, enhancement of phosphoenol pyruvate synthase, enhancement of transhydrogenase, enhancement of the RhtB gene product, enhancement of the RhtC gene product, enhancement of the YfiK gene product, enhancement of a pyruvate carboxylase, and attenuation of acetic acid formation.

It has now been found that microorganisms of the family Enterobacteriaceae after attenuation, in particular after switching off the fruR gene, produce L-amino acids, in particular L-threonine, in an improved way.

The nucleotide sequences of the *Escherichia coli* genes belong to the prior art and may also be obtained from the genome sequence of *Escherichia coli* published by Blattner et al. (Science 277, 1453–1462 (1997)).

The fruR gene is described inter alia by the following data:

| | |
|---|---|
| Designation: | Fructose repressor |
| Reference: | Jahreis et al., Molecular and General Genetics 226, 332–336 (1991) |
| Accession No.: | AE000118 |
| Comment: | The fruR gene is also designated in the prior art as cra gene. |

Apart from the described fruR gene, alleles of the gene may be used that result from the degeneracy of the genetic code or from functionally neutral sense mutations, the activity of the protein not being substantially altered.

In order to achieve an attenuation the expression of the gene or the catalytic properties of the enzyme proteins may for example be reduced or switched off. Optionally both measures may be combined.

The gene expression may be reduced by suitable culture conditions, by genetic alteration (mutation) of the signal structures of the gene expression, or also by antisense-RNA techniques. Signal structures of the gene expression are for example repressor genes, activator genes, operators, promoters, attenuators, ribosome-binding sites, the start codon and terminators. The person skilled in the art may find relevant information in, inter alia, articles by Jensen and Hammer (Biotechnology and Bioengineering 58: 191–195 (1998)), by Carrier and Keasling (Biotechnology Progress 15, 58–64 (1999)), Franch and Gerdes (Current Opinion in Microbiology 3, 159–164 (2000)) and in known textbooks of genetics and molecular biology, such as for example the textbook by Knippers ("Molekulare Genetik", 6$^{th}$ Edition, Georg Thieme Verlag, Stuttgart, Germany, 1995) or that by Winnacker ("Gene und Klone", VCH Verlagsgesellschaft, Weinheim, Germany, 1990).

Mutations that lead to a change or reduction of the catalytic properties of enzyme proteins are known from the prior art. As examples there may be mentioned the works by Qiu and Goodman (Journal of Biological Chemistry 272: 8611–8617 (1997)), Yano et al. (Proceedings of the National Academy of Sciences, USA 95, 5511–5515 (1998)), Wente and Schachmann (Journal of Biological Chemistry 266, 20833–20839 (1991)). Descriptive overviews may be obtained from known textbooks on genetics and molecular biology, such as for example that by Hagemann ("Allgemeine Genetik", Gustav Fischer Verlag, Stuttgart, 1986).

Suitable mutations include transitions, transversions, insertions and deletions. Depending on the action of the amino acid exchange on the enzyme activity, one speaks of missense mutations or nonsense mutations. Insertions or deletions of at least one base pair in a gene lead to frame shift mutations, which in turn lead to the incorporation of false amino acids or the premature termination of a translation. If as a result of the mutation a stop codon is formed in the coding region, this also leads to a premature termination of the translation. Deletions of several codons typically lead to a complete disruption of the enzyme activity. Details regarding the production of such mutations belong to the prior art and may be obtained from known textbooks on genetics and molecular biology, such as for example the textbook by Knippers ("Molekulare Genetik", 6$^{th}$ Edition, Georg Thieme Verlag, Stuttgart, Germany, 1995), that by Winnacker ("Gene und Klone", VCH Verlagsgesellschaft, Weinheim, Germany, 1990) or that by Hagemann ("Allgemeine Genetik", Gustav Fischer Verlag, Stuttgart, 1986).

Suitable mutations in the genes such as for example deletion mutations may be incorporated by gene and/or allele exchange in suitable strains.

A conventional method is the method of gene exchange by means of a conditionally replicating pSC101 derivate pMAK705 described by Hamilton et al. (Journal of Bacteriology 171, 4617–4622 (1989)). Other methods described in the prior art, such as for example that of Martinez-Morales et al. (Journal of Bacteriology 181, 7143–7148 (1999)) or that of Boyd et al. (Journal of Bacteriology 182, 842–847 (2000)) may likewise be used.

It is also possible to transfer mutations in the respective genes or mutations relating to the expression of the relevant genes, by conjugation or transduction into various strains. Furthermore for the production of L-amino acids, in particular L-threonine, using strains of the family Enterobacteriaceae it may be advantageous in addition to the attenuation of the fruR gene also to enhance one or more enzymes of the known threonine biosynthesis pathway or enzymes of anaplerotic metabolism or enzymes for the production of reduced nicotinamide-adenine-dinucleotide phosphate.

The term "enhancement" describes in this connection the raising of the intracellular activity of one or more enzymes or proteins in a microorganism that are coded by the corresponding DNA, by for example increasing the number of copies of the gene or genes, using a strong promoter or a gene that codes for a corresponding enzyme or protein having a high activity, and optionally by combining these measures.

By means of the aforementioned enhancement measures, in particular overexpression, the activity or concentration of the corresponding protein is in general raised by at least 10%, 25%, 50%, 75%, 100%, 150%, 200%, 300%, 400% or 500%, at most up to 1000% or 2000% referred to that of the wild type protein and/or the activity or concentration of the protein in the initial microorganism.

Thus, one or more of the genes selected from the following group may for example by simultaneously enhanced, in particular overexpressed:

the thrABC operon coding for aspartate kinase, homoserine dehydrogenase, homoserine kinase and threonine synthase (U.S. Pat. No. 4,278,765), the pyc gene coding for pyruvate carboxylase (DE-A-19 831 609), the pps gene coding for phosphoenol pyruvate synthase (Molecular and General Genetics 231:332 (1992)), the ppc gene coding for phosphoenol pyruvate carboxylase (Gene 31:279–283 (1984)), the genes pntA and pntB coding for transhydrogenase (European Journal of Biochemistry 158:647–653 (1986)), the gene rhtB imparting homoserine resistance (EP-A-0 994 190), the mqo gene coding for malate:quinone oxidoreductase (DE 100 348 33.5), the gene rhtC imparting threonine resistance (EP-A-1 013 765), and the thrE gene of Corynebacterium glutamicum coding for threonine export (DE 100 264 94.8).

The use of endogenous genes is in general preferred. The term "endogenous genes" or "endogenous nucleotide sequences" is understood to mean the genes or nucleotide sequences present in the population of a species.

Furthermore for the production of L-amino acids, in particular L-threonine, it may be advantageous in addition to the attenuation of the fruR gene also to attenuate, in particular to switch off or reduce the expression of one or more of the genes selected from the following group:

the tdh gene coding for threonine dehydrogenase (Ravnikar and Somerville, Journal of Bacteriology 169, 4716–4721 (1987)), the mdh gene coding for malate dehydrogenase (E.C. 1.1.1.37) (Vogel et al., Archives in Microbiology 149, 36–42 (1987)), the gene product of the open reading frame (orf) yjfA (Accession Number AAC77180 of the National Center for Biotechnology Information (NCBI, Bethesda, Md., USA)), the gene product of the open reading frame (orf) ytfp (Accession Number AAC77179 of the National Center for Biotechnology Information (NCBI, Bethesda, Md., USA)), the pckA gene coding for the enzyme phosphoenol pyruvate carboxykinase (Medina et al. (Journal of Bacteriology 172, 7151–7156 (1990)), the poxB gene coding for pyruvate oxidase (Grabau and Cronan (Nucleic Acids Research 14 (13), 5449–5460 (1986)), the aceA gene coding for isocitrate lyase (EC-No.: 4.1.3.1) (Matsuoko and McFadden; Journal of Bacteriology 170, 4528–4536 (1988) and Accession No.: AE000474), and the dgsA gene coding for the regulator of the phosphotransferase system (Hosono et al., Bioscience, Biotechnology and Biochemistry 59, 256–261 (1995) and Accession No.: AE000255)

Furthermore for the production of L-amino acids, in particular L-threonine, it may be advantageous in addition to the attenuation of the fruR gene also to switch off undesirable secondary reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms produced according to the invention may be cultivated in a batch process (batch cultivation), in a fed batch process (feed process) or in a repeated fed batch process (repetitive feed process). A summary of known cultivation methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Brunswick/Wiesbaden, 1994)).

The culture medium to be used must appropriately satisfy the requirements of the respective strains. Descriptions of culture media of various microorganisms are contained in the handbook "Manual of Methods for General Bacteriology" of the American Society for Bacteriology (Washington D.C., USA, 1981).

As carbon sources, sugars and carbohydrates such as for example glucose, sucrose, lactose, fructose, maltose, molasses, starch and optionally cellulose, oils and fats such as for example soya bean oil, sunflower oil, groundnut oil and coconut oil, fatty acids such as for example palmitic acid, stearic acid and linoleic acid, alcohols such as for example glycerol and ethanol, and organic acids such as for example acetic acid, may be used. These substances may be used individually or as a mixture.

As nitrogen source, organic nitrogen-containing compounds such as peptones, yeast extract, meat extract, malt extract, maize steep liquor, soya bean flour and urea or inorganic compounds such as ammonium sulfate, ammonium chloride, ammonium phosphate, ammonium carbonate and ammonium nitrate may be used. The nitrogen sources may be used individually or as a mixture.

As phosphorus source, phosphoric acid, potassium dihydrogen phosphate or dipotassium hydrogen phosphate or the corresponding sodium-containing salts may be used. The culture medium must furthermore contain salts of metals, such as for example magnesium sulfate or iron sulfate, that are necessary for growth. Finally, essential growth promoters such as amino acids and vitamins may be used in addition to the aforementioned substances. Apart from these, suitable precursors may be added to the culture medium. The aforementioned starting substances may be added to the culture in the form of a single batch or may be metered in in an appropriate manner during the cultivation.

In order to regulate the pH of the culture basic compounds such as sodium hydroxide, potassium hydroxide, ammonia or ammonia water, or acidic compounds such as phosphoric acid or sulfuric acid are used as appropriate. In order to control foam formation antifoaming agents such as for example fatty acid polyglycol esters may be used. In order to maintain the stability of plasmids, suitable selectively acting substances, for example antibiotics, may be added to the medium. In order to maintain aerobic conditions, oxygen or oxygen-containing gas mixtures such as for example air are fed into the culture. The temperature of the culture is normally 25° C. to 45° C., and preferably 30° C. to 40° C. Cultivation is continued until a maximum amount of L-amino acids (or L-threonine) has been formed. This target is normally achieved within 10 hours to 160 hours.

The L-amino acids may be analyzed by anion exchange chromatography followed by ninhydrin derivation, as described by Spackman et al. (Analytical Chemistry, 30, (1958), 1190), or by reversed phase HPLC, as described by Lindroth et al. (Analytical Chemistry (1979) 51: 1167–1174).

The process according to the invention can be used for the enzymatic production of L-amino acids, such as for example L-threonine, L-isoleucine, L-valine, L-methionine, L-homoserine and L-lysine, in particular L-threonine.

A pure culture of the *Escherichia coli* K-12 strain DH5α/pMAK705 was filed as DSM 13720 on 8 Sep. 2000 at the German Collection for Microorganisms and Cell Cultures (DSMZ, Brunswick, Germany) according to the Budapest Convention.

The present invention is described in more detail hereinafter with the aid of examples of implementation.

The isolation of plasmid DNA from *Escherichia coli* as well as all techniques for the restriction, ligation, Klenow treatment and alkaline phosphatase treatment are carried out according to Sambrook et al. (Molecular Cloning—A Laboratory Manual (1989) Cold Spring Harbor Laboratory Press). The transformation of *Escherichia coli* is, unless otherwise described, carried out according to Chung et al. (Proceedings of the National Academy of Sciences of the United States of America, USA (1989) 86: 2172–2175).

The incubation temperature in the production of strains and transformants is 37° C. In the gene exchange process according to Hamilton et al, temperatures of 30° C. and 44° C. are used.

EXAMPLES

Having generally described this invention, a further understanding can be obtained by reference to certain specific examples which are provided herein for purposes of illustration only and are not intended to be limiting unless otherwise specified.

Example 1

Construction of the Deletion Mutation of the fruR Gene

Parts of the gene regions and parts of the 5'- and 3'-region of the fruR gene from *Escherichia coli* K12 lying upstream and downstream of the fruR gene are amplified using the polymerase chain reaction (PCR) as well as synthetic oligonucleotides. Starting from the nucleotide sequence of the fruR gene and sequences in *E. coil* K12 MG1655 DNA (SEQ ID No. 1, Accession Number AE000118) lying upstream and downstream, the following PCR primers are synthesized (MWG Biotech, Ebersberg, Germany):

```
fruR'5'-1:5'-ATGAATCAGGCGCGTTATCC-3'    (SEQ ID No.3)

fruR'5'-2:5'-TTGTCGCTCACACGGTATTG-3'    (SEQ ID No.4)

fruR'3'-1:5'-AGCGTGTGCTGGAGATTGTC-3'    (SEQ ID No.5)

fruR'3'-2:5'-AGCCAGTCACAAGGCATACC-3';   (SEQ ID No.6)
```

SEQ ID No. 2 shows the coding sequence of CDS of the polynucleotide sequence of SEQ ID No. 1.

The chromosomal *E. coli* K12 MG1655 DNA used for the PCR is isolated according to the manufacturer's instructions using "Qiagen Genomic-tips 100/G" (QIAGEN, Hilden, Germany). A ca. 750 bp large DNA fragment from the 5' region of the fruR gene region (designated fruR1) and a ca. 650 bp large DNA fragment from the 3' region of the fruR gene region (designated as fruR2) may be amplified with the specific primers under standard PCR conditions (Innis et al. (1990) PCR Protocols. A Guide to Methods and Applications, Academic Press) with the taq-DNA-polymerase (Gibco-BRL, Eggenstein, Germany). The PCR products are ligated according to the manufacturer's instructions in each case with the vector pCR2.1TOPO (TOPO TA Cloning Kit, Invitrogen, Groningen, Netherlands) and transformed in the *E. coli* strain TOP10F'. The selection of plasmid-carrying cells is carried out on LB agar to which 50 μg/ml of ampicillin has been added. After the plasmid DNA isolation the vector pCR2.1TOPOfruR2 is cleaved with the restriction enzyme NotI and the supernatant 3'-ends are treated with Klenow enzyme. After the restriction with the enzyme SpeI the fruR2 fragment is separated in 0.8% agarose gel and isolated using the QIAquick Gel Extraction Kit (QIAGEN, Hilden, Germany). After the plasmid DNA isolation, the vector pCR2.1TOPOfruR1 is cleaved with the enzymes EcoRV and XbaI and ligated with the isolated fruR2 fragment. The *E. coli* strain DH5α is transformed with the ligation batch and plasmid-carrying cells are selected on LB agar to which 50 μg/ml of ampicillin has been added. After the plasmid DNA isolation those plasmids in which the mutagenic DNA sequence illustrated in SEQ ID No. 7 is

Example 2

Construction of the Exchange Vector pMAK705ΔfruR

The fruR allele described in Example 1 is isolated from the vector pCR2.1TOPOΔfruR after restriction with the enzyme EcoO109I, treatment of the supernatant 3'-ends with Klenow enzyme, restriction with the enzyme BamHI and separation in 0.8% agarose gel, and ligated with the plasmid pMAK705 (Hamilton et al. (1989) Journal of Bacteriology 171, 4617–4622) that has been digested with the enzymes HincII and BamHI. The ligation batch is transformed in DH5α and plasmid-carrying cells are selected on LB agar to which 20 µg/ml chloramphenicol had been added. Successful cloning is detected after plasmid DNA isolation and cleavage with the enzymes HindIII, BamHI, EcoRV, ScaI and SpeI. The resultant exchange vector pMAK705ΔfruR (=pMAK705deltafruR) is shown in FIG. 1.

Example 3

Site-Specific Mutagenesis of the fruR Gene in the E. coli Strain MG442

The E. coli strain MG442 producing L-threonine is described in patent specification U.S. Pat. No. 4,278,765 and is filed as CMIM B-1628 at the Russian National Collection for Industrial Microorganisms (VKPM, Moscow, Russia).

For the exchange of the chromosomal fruR gene by the plasmid-coded deletion construct, MG442 is transformed with the plasmid pMAK705ΔfruR. The gene exchange is carried out by the selection process described by Hamilton et al. (1989) Journal of Bacteriology 171, 4617–4622) and is verified by standard PCR methods (Innis et al. (1990) PCR Protocols. A guide to methods and applications, Academic Press) with the following oligonucleotide primers:

```
fruR'5'-1:  5'-ATGAATCAGGCGCGTTATCC-3' (SEQ ID No.3)

fruR'3'-2:  5'-AGCCAGTCACAAGGCATACC-3' (SEQ ID No.6)
```

After exchange has been carried out the form of the ΔfruR allele illustrated in SEQ ID No. 8 is present in MG442. The resultant strain is designated MG442ΔfruR.

Example 4

Production of L-Threonine Using the Strain MG442ΔfruR

MG442ΔfruR is cultivated on minimal medium having the following composition: 3.5 g/l $Na_2HPO_4.2H_2O$, 1.5 g/l $KH_2PO_4$, 1 g/l $NH_4Cl$, 0.1 g/l $MgSO_4.7H_2O$, 2 g/l glucose and 20 g/l agar. The formation of L-threonine is checked in batch cultures of 10 ml that are contained in 100 ml Erlenmeyer flasks. For this, 10 ml of preculture medium of the following composition: 2 g/l yeast extract, 10 g/l $(NH_4)_2SO_4$, 1 g/l $KH_2PO_4$, 0.5 g/l $MgSO_4.7H_2O$, 15 g/l $CaCO_3$, 20 g/l glucose are inoculated and incubated for 16 hours at 37° C. and 180 rpm in an ESR incubator from Kühner AG (Birsfelden, Switzerland). 250 µl of this preculture are reinoculated in 10 ml of production medium (25 g/l $(NH_4)_2SO_4$, 2 g/l $KH_2PO_4$, 1 g/l $MgSO_4.7H_2O$, 0.03 g/l $FeSO_4.7H_2O$, 0.018 g/l $MnSO_4.1H_2O$, 30 g/l $CaCO_3$ and 20 g/l glucose) and incubated for 48 hours at 37° C. After incubation the optical density (OD) of the culture suspension is measured with an LP2W photometer from the Dr. Lange company (Dusseldorf, Germany) at a measurement wavelength of 660 nm.

The concentration of formed L-threonine is then determined in the sterile-filtered culture supernatant using an amino acid analyzer from Eppendorf-BioTronik (Hamburg, Germany) by ion exchange chromatography and post-column reaction with ninhydrin detection.

The result of the test is given in Table 1.

TABLE 1

| Strain | OD (660 nm) | L-Threonin g/l |
|---|---|---|
| MG442 | 6.0 | 1.5 |
| MG442ΔfruR | 6.3 | 1.7 |

Obviously, numerous modifications and variations of the present invention are possible in light of the above teachings. It is therefore to be understood that within the scope of the appended claims, the invention may be practiced otherwise than as specifically described herein.

The publications cited herein are incorporated herein by reference.

This application is based on German Patent Application Serial No. 101 16 518.8, filed on Apr. 3, 2001, and incorporated herein by reference in its entirety.

What is claimed is:

1. A process for producing an L-amino acid comprising:
   a) culturing a modified enterobacterium of the genus *Escherichia* in a medium for a time and under conditions suitable for producing said L-amino acid, and
   b) recovering or isolating said L-amino acid,
   wherein expression of the fruR (cra) gene has been eliminated from said modified *Escherichia* by deleting all or part of the fruR gene,
   wherein said fruR (cra) gene is obtainable from Escherichia by PCR amplification using primer fruR'5'-1 (SEQ ID NO: 3) and primer fruR'3'-2 (SEQ ID NO: 6).

2. The process of claim 1, wherein said fruR (cra) gene encodes the polypeptide of SEQ ID NO: 2.

3. The process of claim 1, wherein said fruR (cra) gene is described by SEQ ID NO: 1.

4. The process of claim 1, wherein the L-amino-acid is selected from the group consisting of L-asparagine, L-glutamate, L-glycine, L-alanine, L-cysteine, L-leucine, L-tyrosine, L-phenylalanine, L-histidine, L-tryptophan and L-arginine.

5. The process of claim 1, wherein the L-amino-acid is selected from the group consisting of L-serine, L-homoserine, L-valine, L-methionine, L isoleucine, and L-lysine.

6. The process of claim 1, wherein said L-amino acid is L-threonine.

7. The process of claim 1, wherein constituents of the fermentation broth and/or the biomass in its entirety or portions thereof remain in the isolated L-amino acid.

8. The process of claim 1, wherein the modified *Escherichia* further comprises at least one overexpressed gene product compared to the unmodified *Escherichia*, wherein the gene product is encoded by a gene selected from the group consisting of:
   at least one gene of a thrABC operon, wherein said at least one gene codes for aspartate kinase, homoserine dehydrogenase, homoserine kinase and threonine synthase,
   the Corynebacterium glutamicum gene coding for pyruvate carboxylase,
   a gene coding for phosphoenol pyruvate synthase,
   gene coding for phosphoenol pyruvate carboxylase,
   a pntA and a pntB gene coding for the subunits of pyridine transhydrogenase,
   the *Escherichia coli* rhtB gene coding for a protein imparting homoserine resistance,
   a gene coding for malate:quinone oxidoreductase,
   the *Escherichia coil* rhtC gene coding for a protein imparting threonine resistance, and
   the *Corynebacterium glutamicum* gene coding for a threonine export carrier protein.

9. The process of claim 1, wherein the modified *Escherichia* further comprises at least one gene whose expression has been eliminated compared to the unmodified *Escherichia*, wherein the at least one gene is selected from the group consisting of:
- a gene coding for threonine dehydrogenase,
- a gene coding for malate dehydrogenase,
- a gene coding for phosphoenol pyruvate carboxykinase,
- a gene coding for pyruvate oxidase,
- a gene coding for isocitrate lyase, and
- a gene coding for a DgsA protein, a regulator of the phosphotransferase system.

10. The process of claim 1, wherein said *Escherichia* is *Escherichia coli*.

11. The process of claim 1, wherein the expression of the fruR (cra) gene has been eliminated by the deletion of all of the fruR (cra) gene.

12. The process of claim 1, wherein the L-amino acid is recovered from the modified *Escherichia*.

13. The process of claim 1, wherein the L-amino acid is recovered from the medium.

14. The process of claim 1, wherein culturing is continued until a maximum amount of the L-amino acid has been formed.

15. The process of claim 1 wherein culturing is performed using a batch process.

16. The process of claim 1, wherein culturing is performed using a fed-batch process.

17. The process of claim 1, wherein culturing is performed using a repeated fed batch process.

18. The process of claim 1, wherein the modified *Escherichia* is *Escherichia coil* (*E. coli*) and said *Escherichia coli* comprises at least one gene whose expression has been eliminated compared to the unmodified *Escherichia coli*, wherein the at least one gene is selected from the group consisting of:
- the open reading frame (orf) yjfA of *E. coli*, and
- the open reading frame(orf) ytfP of *E. coli*.

* * * * *

SEQUENCE LISTING

```
<160> NUMBER OF SEQ ID NOS: 8

<210> SEQ ID NO 1
<211> LENGTH: 2166
<212> TYPE: DNA
<213> ORGANISM: Escherichia coli
<220> FEATURE:
<221> NAME/KEY: CDS
<222> LOCATION: (641)..(1645)
<223> OTHER INFORMATION:
```

<400> SEQUENCE: 1

```
atgaatcagg cgcgttatcc cgcgtgattg gccttttttc ccagcgtggc tacaacattg      60
aaagcctgac cgttgcgcca accgacgatc cgacattatc gcgtatgacc atccagaccg     120
tgggcgatga aaaagtactt gagcagatcg aaaagcaatt acacaaactg gtcgatgtct     180
tgcgcgtgag tgagttgggg cagggcgcgc atgttgagcg ggaaatcatg ctggtgaaaa     240
ttcaggccag cggttacggg cgtgacgaag tgaaacgtaa tacggaaata ttccgtgggc     300
aaattatcga tgtcacaccc tcgctttata ccgttcaatt agcaggcacc agcggtaagc     360
ttgatgcatt tttagcatcg attcgcgatg tggcgaaaat tgtggaggtt gctcgctctg     420
gtgtggtcgg actttcgcgc ggcgataaaa taatgcgttg agaatgatct caatgcgcaa     480
tttacagccc aacatgtcac gttgggcttt ttttgcgaaa tcagtgggaa cctgaataa     540 aagcagttgc cgcagttaat tttctgcgct agatgttaa tgaatttaac ccataccagt     600
acaatggcta tggttttac attttacgca aggggcaatt gtg aaa ctg gat gaa      655
                                            Val Lys Leu Asp Glu
                                             1               5
```

| | | | | | | | | | | | | | | | | |
|---|---|---|---|---|---|---|---|---|---|---|---|---|---|---|---|---|
| atc | gct | cgg | ctg | gcg | gga | gtg | tcg | cgg | acc | act | gca | agc | tat | gtt | att | 703 |
| Ile | Ala | Arg | Leu | Ala | Gly | Val | Ser | Arg | Thr | Thr | Ala | Ser | Tyr | Val | Ile | |
| | | | 10 | | | | 15 | | | | | 20 | | | | |

```
aac ggc aaa gcg aag caa tac cgt gtg agc gac aaa acc gtt gaa aaa      751
Asn Gly Lys Ala Lys Gln Tyr Arg Val Ser Asp Lys Thr Val Glu Lys
         25                  30                  35 gtc atg gct gtg gtg cgt gag cac aat tac cac ccg aac gcc gtg gca      799
Val Met Ala Val Val Arg Glu His Asn Tyr His Pro Asn Ala Val Ala
         40                  45                  50 gct ggg ctt cgt gct gga cgc aca cgt tct att ggt ctt gtg atc ccc      847
Ala Gly Leu Arg Ala Gly Arg Thr Arg Ser Ile Gly Leu Val Ile Pro
55                  60                  65 gat ctg gag aac acc agc tat acc cgc atc gct aac tat ctt gaa cgc      895
Asp Leu Glu Asn Thr Ser Tyr Thr Arg Ile Ala Asn Tyr Leu Glu Arg
70                  75                  80                  85 cag gcg cgg caa cgg ggt tat caa ctg ctg att gcc tgc tca gaa gat      943
Gln Ala Arg Gln Arg Gly Tyr Gln Leu Leu Ile Ala Cys Ser Glu Asp
             90                  95                 100 cag cca gac aac gaa atg cgg tgc att gag cac ctt tta cag cgt cag      991
Gln Pro Asp Asn Glu Met Arg Cys Ile Glu His Leu Leu Gln Arg Gln
            105                 110                 115 gtt gat gcc att att gtt tcg acg tcg ttg cct cct gag cat cct ttt     1039
Val Asp Ala Ile Ile Val Ser Thr Ser Leu Pro Pro Glu His Pro Phe
        120                 125                 130 tat caa cgc tgg gct aac gac ccg ttc ccg att gtc gcg ctg gac cgc     1087
Tyr Gln Arg Trp Ala Asn Asp Pro Phe Pro Ile Val Ala Leu Asp Arg
    135                 140                 145 gcc ctc gat cgt gaa cac ttc acc agc gtg gtt ggt gcc gat cag gat     1135
Ala Leu Asp Arg Glu His Phe Thr Ser Val Val Gly Ala Asp Gln Asp
150                 155                 160                 165 gat gcc gaa atg ctg gcg gaa gag tta cgt aag ttt ccc gcc gag acg     1183
Asp Ala Glu Met Leu Ala Glu Glu Leu Arg Lys Phe Pro Ala Glu Thr
                170                 175                 180 gtg ctt tat ctt ggt gcg cta ccg gag ctt tct gtc agc ttc ctg cgt     1231
Val Leu Tyr Leu Gly Ala Leu Pro Glu Leu Ser Val Ser Phe Leu Arg
            185                 190                 195 gaa caa ggt ttc cgt act gcc tgg aaa gat gat ccg cgc gaa gtg cat     1279
Glu Gln Gly Phe Arg Thr Ala Trp Lys Asp Asp Pro Arg Glu Val His
        200                 205                 210
```

-continued

```
ttc ctg tat gcc aac agc tat gag cgg gag gcg gct gcc cag tta ttc      1327
Phe Leu Tyr Ala Asn Ser Tyr Glu Arg Glu Ala Ala Ala Gln Leu Phe
    215                 220                 225 gaa aaa tgg ctg gaa acg cat ccg atg ccg cag gcg ctg ttc aca acg      1375
Glu Lys Trp Leu Glu Thr His Pro Met Pro Gln Ala Leu Phe Thr Thr
230                 235                 240                 245 tcg ttt gcg ttg ttg caa gga gtg atg gat gtc acg ctg cgt cgc gac      1423
Ser Phe Ala Leu Leu Gln Gly Val Met Asp Val Thr Leu Arg Arg Asp
                250                 255                 260 ggc aaa ctg cct tct gac ctg gca att gcc acc ttt ggc gat aac gaa      1471
Gly Lys Leu Pro Ser Asp Leu Ala Ile Ala Thr Phe Gly Asp Asn Glu
            265                 270                 275 ctg ctc gac ttc tta cag tgt ccg gtg ctg gca gtg gct caa cgt cac      1519
Leu Leu Asp Phe Leu Gln Cys Pro Val Leu Ala Val Ala Gln Arg His
        280                 285                 290 cgc gat gtc gca gag cgt gtg ctg gag att gtc ctg gca agc ctg gac      1567
Arg Asp Val Ala Glu Arg Val Leu Glu Ile Val Leu Ala Ser Leu Asp
    295                 300                 305 gaa ccg cgt aag cca aaa cct ggt tta acg cgc att aaa cgt aat ctc      1615
Glu Pro Arg Lys Pro Lys Pro Gly Leu Thr Arg Ile Lys Arg Asn Leu
310                 315                 320                 325 tat cgc cgc ggc gtg ctc agc cgt agc taa gccgcgaaca aaatacgcg         1665
Tyr Arg Arg Gly Val Leu Ser Arg Ser
                330 ccaggtgaat ttccctctgg cgcgtagagt acgggactgg acatcaatat gcttaaagta    1725 aataagacta ttcctgacta ttattgataa atgcttttaa acccgcccgt taattaactc    1785 accagctgaa attcacaata attaagtgat atcgacagcg cgttttttgca ttattttgtt   1845 acatgcggcg atgaattgcc gatttaacaa acactttttct ttgcttttgc gcaaacccgc   1905 tggcatcaag cgccacacag acgtaacaag gactgttaac cggggaagat atgtcctaaa    1965 atgccgctcg cgtcgcaaac tgacacttta tatttgctgt ggaaaatagt gagtcatttt    2025 aaaacggtga tgacgatgag ggattttttc ttacagctat tcataacgtt aatttgcttc    2085 gcacgttgga cgtaaaataa acaacgctga tattagccgt aaacatcggg ttttttacct    2145 cggtatgcct tgtgactggc t                                              2166
```

<210> SEQ ID NO 2
<211> LENGTH: 334
<212> TYPE: PRT
<213> ORGANISM: Escherichia coli

<400> SEQUENCE: 2

```
Val Lys Leu Asp Glu Ile Ala Arg Leu Ala Gly Val Ser Arg Thr Thr
1               5                   10                  15

Ala Ser Tyr Val Ile Asn Gly Lys Ala Lys Gln Tyr Arg Val Ser Asp
                20                  25                  30

Lys Thr Val Glu Lys Val Met Ala Val Val Arg Glu His Asn Tyr His
            35                  40                  45

Pro Asn Ala Val Ala Ala Gly Leu Arg Ala Gly Arg Thr Arg Ser Ile
        50                  55                  60

Gly Leu Val Ile Pro Asp Leu Glu Asn Thr Ser Tyr Thr Arg Ile Ala
65                  70                  75                  80

Asn Tyr Leu Glu Arg Gln Ala Arg Gln Arg Gly Tyr Gln Leu Leu Ile
                85                  90                  95

Ala Cys Ser Glu Asp Gln Pro Asp Asn Glu Met Arg Cys Ile Glu His
                100                 105                 110
```

```
Leu Leu Gln Arg Gln Val Asp Ala Ile Ile Val Ser Thr Ser Leu Pro
        115                 120                 125

Pro Glu His Pro Phe Tyr Gln Arg Trp Ala Asn Asp Pro Phe Pro Ile
130                 135                 140

Val Ala Leu Asp Arg Ala Leu Asp Arg Glu His Phe Thr Ser Val Val
145                 150                 155                 160

Gly Ala Asp Gln Asp Asp Ala Glu Met Leu Ala Glu Leu Arg Lys
                165                 170                 175

Phe Pro Ala Glu Thr Val Leu Tyr Leu Gly Ala Leu Pro Glu Leu Ser
                180                 185                 190

Val Ser Phe Leu Arg Glu Gln Gly Phe Arg Thr Ala Trp Lys Asp Asp
        195                 200                 205

Pro Arg Glu Val His Phe Leu Tyr Ala Asn Ser Tyr Glu Arg Glu Ala
210                 215                 220

Ala Ala Gln Leu Phe Glu Lys Trp Leu Glu Thr His Pro Met Pro Gln
225                 230                 235                 240

Ala Leu Phe Thr Thr Ser Phe Ala Leu Leu Gln Gly Val Met Asp Val
                245                 250                 255

Thr Leu Arg Arg Asp Gly Lys Leu Pro Ser Asp Leu Ala Ile Ala Thr
                260                 265                 270

Phe Gly Asp Asn Glu Leu Leu Asp Phe Leu Gln Cys Pro Val Leu Ala
                275                 280                 285

Val Ala Gln Arg His Arg Asp Val Ala Glu Arg Val Leu Glu Ile Val
                290                 295                 300

Leu Ala Ser Leu Asp Glu Pro Arg Lys Pro Lys Pro Gly Leu Thr Arg
305                 310                 315                 320

Ile Lys Arg Asn Leu Tyr Arg Arg Gly Val Leu Ser Arg Ser
                325                 330

<210> SEQ ID NO 3
<211> LENGTH: 20
<212> TYPE: DNA
<213> ORGANISM: Artificial sequence
<220> FEATURE:
<223> OTHER INFORMATION: Synthetic DNA

<400> SEQUENCE: 3
atgaatcagg cgcgttatcc                                              20

<210> SEQ ID NO 4
<211> LENGTH: 20
<212> TYPE: DNA
<213> ORGANISM: Artificial sequence
<220> FEATURE:
<223> OTHER INFORMATION: Synthetic DNA

<400> SEQUENCE: 4
ttgtcgctca cacggtattg                                              20

<210> SEQ ID NO 5
<211> LENGTH: 20
<212> TYPE: DNA
<213> ORGANISM: Artificial sequence
<220> FEATURE:
<223> OTHER INFORMATION: Synthetic DNA

<400> SEQUENCE: 5
agcgtgtgct ggagattgtc                                              20
```

-continued

<210> SEQ ID NO 6
<211> LENGTH: 20
<212> TYPE: DNA
<213> ORGANISM: Artificial sequence
<220> FEATURE:
<223> OTHER INFORMATION: Synthetic DNA

<400> SEQUENCE: 6
agccagtcac aaggcatacc                                                    20

<210> SEQ ID NO 7
<211> LENGTH: 1512
<212> TYPE: DNA
<213> ORGANISM: Escherichia coli
<220> FEATURE:
<221> NAME/KEY: misc_feature
<222> LOCATION: (1)..(42)
<223> OTHER INFORMATION: Technical DNA/ remainder polylinker sequence
<221> NAME/KEY: misc_feature
<222> LOCATION: (43)..(780)
<223> OTHER INFORMATION: Part of the upstream-lying region and part of
      the 5'-region of the fruR gene
<221> NAME/KEY: misc_feature
<222> LOCATION: (781)..(837)
<223> OTHER INFORMATION: Technical DNA/ remainder polylinker sequence
<221> NAME/KEY: misc_feature
<222> LOCATION: (838)..(1471)
<223> OTHER INFORMATION: Part of the 3'-region of the fruR gene and part
      of the downstream-lying region
<221> NAME/KEY: misc_feature
<222> LOCATION: (1472)..(1512)
<223> OTHER INFORMATION: Technical DNA/ remainder polylinker sequence

<400> SEQUENCE: 7
gatccactag taacggccgc cagtgtgctg gaattcgccc ttatgaatca ggcgcgttat        60
cccgcgtgat tggccttttt tcccagcgtg gctacaacat tgaaagcctg accgttgcgc      120
caaccgacga tccgacatta tcgcgtatga ccatccagac cgtgggcgat gaaaaagtac      180
ttgagcagat cgaaaagcaa ttacacaaac tggtcgatgt cttgcgcgtg agtgagttgg      240
ggcagggcgc gcatgttgag cgggaaatca tgctggtgaa aattcaggcc agcggttacg      300
ggcgtgacga agtgaaacgt aatacggaaa tattccgtgg gcaaattatc gatgtcacac      360
cctcgcttta taccgttcaa ttagcaggca ccagcggtaa gcttgatgca ttttttagcat     420 cgattcgcga tgtggcgaaa attgtggagg ttgctcgctc tggtgtggtc ggactttcgc      480
gcggcgataa aataatgcgt tgagaatgat ctcaatgcgc aatttacagc ccaacatgtc      540
acgttgggct ttttttgcga aatcagtggg aacctggaat aaaagcagtt gccgcagtta      600
attttctgcg cttagatgtt aatgaattta acccatacca gtacaatggc tatggttttt      660
acattttacg caaggggcaa ttgtgaaact ggatgaaatc gctcggctgg cgggagtgtc      720
gcggaccact gcaagctatg ttattaacgg caaagcgaag caataccgtg tgagcgacaa      780
aagggcgaat tctgcagatg gccgccagtg tgatggatat ctgcagaatt cgcccttagc      840
gtgtgctgga gattgtcctg gcaagcctgg acgaaccgcg taagccaaaa cctggtttaa      900
cgcgcattaa acgtaatctc tatcgccgcg gcgtgctcag ccgtagctaa gccgcgaaca      960
aaaatacgcg ccaggtgaat ttccctctgg cgcgtagagt acgggactgg acatcaatat     1020
gcttaaagta aataagacta ttcctgacta ttattgataa atgcttttaa acccgcccgt     1080
taattaactc accagctgaa attcacaata attaagtgat atcgacagcg cgttttttgca    1140 ttatttttgtt acatgcggcg atgaattgcc gatttaacaa acactttttct ttgcttttgc    1200 gcaaacccgc tggcatcaag cgccacacag acgtaacaag gactgttaac cggggaagat     1260

-continued

```
atgtcctaaa atgccgctcg cgtcgcaaac tgacacttta tatttgctgt ggaaaatagt      1320
gagtcatttt aaaacggtga tgacgatgag ggatttttc ttacagctat tcataacgtt       1380
aatttgcttc gcacgttgga cgtaaaataa acaacgctga tattagccgt aaacatcggg      1440 tttttaact cggtatgcct tgtgactggc taagggcgaa ttccagcaca ctggcggccg       1500
ttactagagg gc                                                           1512
```

<210> SEQ ID NO 8
<211> LENGTH: 268
<212> TYPE: DNA
<213> ORGANISM: Escherichia coli
<220> FEATURE:
<221> NAME/KEY: misc_feature
<222> LOCATION: (1)..(3)
<223> OTHER INFORMATION: start codon of the delta fruR allele
<221> NAME/KEY: misc_feature
<222> LOCATION: (1)..(98)
<223> OTHER INFORMATION: 5'-region of the delta fruR allele
<221> NAME/KEY: misc_feature
<222> LOCATION: (99)..(155)
<223> OTHER INFORMATION: Technical DNA/ remainder polylinker sequence
<221> NAME/KEY: misc_feature
<222> LOCATION: (156)..(265)
<223> OTHER INFORMATION: 3'-region of the delta fruR allele
<221> NAME/KEY: misc_feature
<222> LOCATION: (266)..(268)
<223> OTHER INFORMATION: stop codon of the delta fruR allele

<400> SEQUENCE: 8

```
gtgaaactgg atgaaatcgc tcggctggcg ggagtgtcgc ggaccactgc aagctatgtt       60
attaacggca aagcgaagca ataccgtgtg agcgacaaaa gggcgaattc tgcagatggc      120
cgccagtgtg atggatatct gcagaattcg cccttagcgt gtgctggaga ttgtcctggc      180
aagcctggac gaaccgcgta agccaaaacc tggtttaacg cgcattaaac gtaatctcta      240
tcgccgcggc gtgctcagcc gtagctaa                                         268
```